(12) United States Patent
Huang et al.

(10) Patent No.: US 11,172,569 B2
(45) Date of Patent: Nov. 9, 2021

(54) STRIP FOR AN ELECTRONIC DEVICE AND MANUFACTURING METHOD THEREOF

(71) Applicant: TAI-SAW Technology Co., Ltd., Taoyuan (TW)

(72) Inventors: Yu-Tung Huang, Taoyuan (TW); Ming-Hung Chang, Taoyuan (TW); Szu-Heng Liu, Taoyuan (TW); You-Jen Cho, Taoyuan (TW); Yi-Qi Huang, Taoyuan (TW); Chun Kuo, Taoyuan (TW)

(73) Assignee: TAI-SAW Technology Co., Ltd., Taoyuan (TW)

(*) Notice: Subject to any disclaimer, the term of this patent is extended or adjusted under 35 U.S.C. 154(b) by 0 days.

(21) Appl. No.: 15/718,507

(22) Filed: Sep. 28, 2017

(65) Prior Publication Data
US 2018/0027649 A1    Jan. 25, 2018

Related U.S. Application Data

(63) Continuation-in-part of application No. 14/588,321, filed on Dec. 31, 2014, now Pat. No. 9,807,888.

(30) Foreign Application Priority Data

Dec. 31, 2013    (TW) ................. 102149389

(51) Int. Cl.
*H05K 1/02*    (2006.01)
*H05K 3/10*    (2006.01)
(Continued)

(52) U.S. Cl.
CPC .......... *H05K 1/0272* (2013.01); *G01N 31/00* (2013.01); *G01N 33/18* (2013.01);
(Continued)

(58) Field of Classification Search
CPC .... H05K 13/0469; H05K 1/02; H05K 1/0296; H05K 3/02; H05K 3/305;
(Continued)

(56) References Cited

U.S. PATENT DOCUMENTS 6,566,611 B2    5/2003  Kochanowski et al.
2009/0283611 A1*  11/2009  Varanasi ................. B05B 7/066
                                                      239/366
(Continued)

OTHER PUBLICATIONS

Yokomaku et al., "Electrowetting on gold electrodes with microscopic three-dimensional structures for microfluidic devices," J. Appl. Physics, 2008, 104:064910-1 to 064910-8.*

*Primary Examiner* — Ahmed N Sefer
(74) *Attorney, Agent, or Firm* — The PL Law Group, PLLC

(57) ABSTRACT

A strip for an electronic device senses a liquid sample. The strip includes a substrate having a first surface, a plurality of protrusions disposed on the first surface, and each having a width, and a hydrophilic layer having a layer surface disposed on the first surface and the plurality of protrusions, and having a second surface opposite to the layer surface, whereby the liquid sample and the second surface have a contact angle therebetween ranging from 2 to 85 degrees when the liquid sample is disposed on the hydrophilic layer.

17 Claims, 15 Drawing Sheets

(51) Int. Cl.
*G01N 33/487* (2006.01)
*G01N 31/00* (2006.01)
*G01N 33/18* (2006.01)
*H05K 3/30* (2006.01)
*H01L 23/498* (2006.01)
*H01L 23/00* (2006.01)
*H01L 23/15* (2006.01)
*H05K 1/11* (2006.01)

(52) U.S. Cl.
CPC .. *G01N 33/48707* (2013.01); *H01L 23/49811* (2013.01); *H01L 23/49827* (2013.01); *H05K 3/10* (2013.01); *H05K 3/305* (2013.01); *H01L 23/15* (2013.01); *H01L 24/13* (2013.01); *H01L 24/81* (2013.01); *H01L 2224/1319* (2013.01); *H01L 2224/16237* (2013.01); *H01L 2224/81192* (2013.01); *H01L 2224/81385* (2013.01); *H01L 2224/81439* (2013.01); *H01L 2224/81444* (2013.01); *H01L 2224/81447* (2013.01); *H05K 1/111* (2013.01); *H05K 2201/0302* (2013.01); *H05K 2201/0373* (2013.01); *H05K 2201/09781* (2013.01); *Y02P 70/50* (2015.11); *Y10T 156/10* (2015.01)

(58) Field of Classification Search
CPC ........ H05K 2201/09045; H05K 1/0272; H01L 23/49827; H01L 23/49811
See application file for complete search history.

(56) References Cited

U.S. PATENT DOCUMENTS

| | | | | |
|---|---|---|---|---|
| 2011/0300345 | A1* | 12/2011 | Bessonov | B82Y 10/00 428/195.1 |
| 2012/0156773 | A1* | 6/2012 | Smith | C12N 5/0068 435/350 |
| 2012/0302465 | A1* | 11/2012 | Elmouelhi | B01J 20/268 506/20 |
| 2013/0142994 | A1* | 6/2013 | Wang | C03C 15/00 428/141 |
| 2014/0205805 | A1* | 7/2014 | Takihara | G02B 1/105 428/142 |
| 2015/0357220 | A1* | 12/2015 | Momikura | H01L 21/6875 361/234 |

* cited by examiner

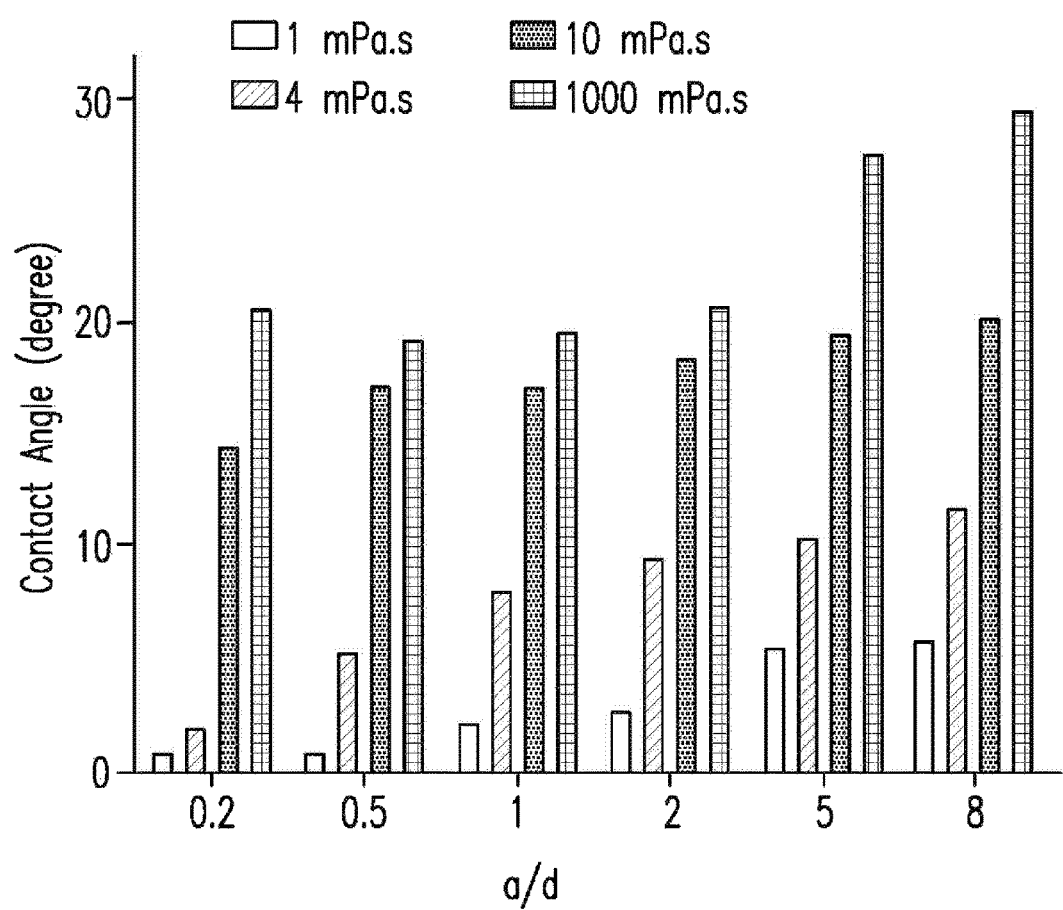

STRIP FOR AN ELECTRONIC DEVICE AND MANUFACTURING METHOD THEREOF

CROSS-REFERENCE TO RELATED APPLICATION AND CLAIM OF PRIORITY

This application is a Continuation-In-Part of co-pending application Ser. No. 14/588,321 filed on Dec. 31, 2014, and for which priority is claimed under 35 U.S.C. § 120; and this application claims priority of Application No. 102149389 filed in Taiwan on Dec. 31, 2013 under 35 U.S.C. § 119; the entire contents of all are hereby incorporated by reference.

FIELD OF THE INVENTION

The present invention relates to a packaging technology for an electronic device, and more particularly to a conducting package structure and a manufacturing method thereof.

BACKGROUND OF THE INVENTION

As technology advances, electronic devices become smaller, and this raises requirements for electronic packaging technology and assembly quality. A variety of new packaging technologies are gradually being developed, and recently new industries for electronic packaging have appeared.

The electronic packaging is to protect electronic devices and circuits from influences in the external environment, which includes physical and chemical influences. That is, it isolates the external environment using a protective layer to protect the electronic devices. The electronic packaging means a manufacturing process that a variety of electronic devices are assembled and connected on demand when producing electronic apparatuses. The electronic packaging has the effect of power distribution, signal distribution, heat dissipation, protective packaging and enhancement of mechanical strength of the apparatus, and furthermore physical and electric connections of circuits and systems in electronic devices. The types of electronic packaging may be classified into metal packages, ceramic packages and plastic packages according to the material; pre-mold packages and post-mold packages according to the technique; and Single Inline Package (SIP), Dual Inline Package (DIP), Plastic Leaded Chip Carrier (PLCC), Quad Flat No Leads (QFP), Chip-Size Package (CSP), etc. according to the package housing.

The present invention is a packaging technology applicable to an electronic device, wherein the processes for the electronic package may be classified into level 1 to 4 packages. Level 1 package is a process to assemble an exposed IC chip to form a first electronic device and cause the IC to have I/Os using an assembly method. The assembly method includes Wire Bonding, Flip Chip, Tape Automatic Bonding, etc. Level 2 package is a process to adhere the first electronic device to a first substrate (e.g., PCB) to form a second electronic device. The adhering methods include Pin Through Hole (PTH) and Surface Mount Technology (SMT). Level 3 package is a process to assemble a second substrate having a plurality of second electronic devices on a motherboard to form a subsystem. Level 4 package is a process to combine subsystems to form a complete electronic product. Objectives of each level of packaging include higher efficiency, smaller size, and lower cost.

Because SMT technology needs no through holes corresponding to the pins of the electronic device, and the size of the electronic device which uses SMT technology is smaller than which uses through-hole package, SMT technology has inevitably become the main technology for more functional and smaller electronic devices.

The packaging process of SMT technology includes solder-paste printing, component placement, and reflow processes. The processes involve very complicated and extensive factors, such as original materials, machinery equipment, parameter setting, production process, and so on. Wherein, the component placement technique involves a dispensing technique and a dot control technique. It is a challenge for one skilled in the art how to stably and efficiently produce high-quality electronic products. The research has revealed that the packaging process for SMT technology requires a great deal of time for process debugging. Thus, how to obtain a stable process is an important task for the packaging process for SMT technology. Based on the past research, it is known that the main reasons for solder defects are the control of the solder-paste printing, the solder quality, the dispensing technique and the dot control technique, which are determined by the accuracy of the component placement, and the stability and reliability of the solder joint structure are determined by the reflow process.

U.S. Pat. No. 6,566,611B2 provides anti-tombstoning structures and methods of manufacture, which reduce asymmetrical and lateral surface-tension forces between devices and a substrate by at least a conducting pad on the patterned substrate. Thereby, the anti-tombstoning due to the asymmetrical and lateral surface-tension forces is not induced during the reflow process. The process of the US patent focused on the stability of the solder joint structure, reducing the tension between the devices and the substrate. However, the US patent did not research the relationship between the glue material and the conducting pads (that is, a conducting structure in the present invention) to further solve problems of adhering accuracy and available yield.

In order to overcome the drawbacks in the prior art, a conducting package structure and a manufacturing method thereof are disclosed. The particular design in the present invention not only solves the problems described above, but is also easy to implement. Thus, the present invention has utility for the industry.

SUMMARY

In accordance with an aspect of the present invention, a method for manufacturing a conducting package is disclosed. The method includes providing a substrate; forming a conducting structure on the substrate, wherein the conducting structure has a surface; patterning the surface to form a patterned surface; dispensing a glue material on the patterned surface, wherein a wetting angle between the glue material and the patterned surface is determined by the patterned surface; and disposing an electronic device on the glue material.

In accordance with another aspect of the present invention, a conducting package structure is disclosed. The conducting package structure includes a substrate, a conducting structure and a glue material, wherein: the conducting structure is formed on the substrate, and has a patterned surface; and the glue material is disposed on the patterned surface, wherein a wetting angle between the glue material and the patterned surface is determined by the patterned surface.

In accordance with a further aspect of the present invention, a conducting package structure is disclosed. The conducting package structure includes a substrate; and a conducting structure having a first surface disposed on the substrate and a second surface formed with a plurality of guide rods, wherein any two adjacent guide rods have therebetween a distance larger than two times the width of any of the two adjacent guide rods.

In accordance with a further aspect of the present invention, a conducting package structure is disclosed. The conducting package structure includes a substrate; and a conducting material formed with a first patterned structure, wherein the first patterned structure has a first surface disposed on the substrate and a second surface opposite to the first surface.

In accordance with a further aspect of the present invention, a strip for an electronic device configured to sense a liquid sample is disclosed. The strip comprises a substrate has a first surface; a plurality of protrusions disposed on the first surface, and each having a width; and a hydrophilic layer having a layer surface disposed on the first surface and the plurality of protrusions, and having a second surface opposite to the layer surface, whereby the liquid sample and the second surface have a contact angle therebetween ranging from 2 to 85 degrees when the liquid sample is disposed on the hydrophilic layer.

In accordance with a further aspect of the present invention, a strip for an electronic device configured to sense a liquid sample is disclosed. The strip comprises a substrate having a first surface; and a hydrophilic layer disposed on the first surface, and having a plurality of protrusions, wherein: each of the plurality of protrusions has a width, and any adjacent two of the plurality of protrusions have a distance therebetween ranging from 0.5 to 100 times of the width.

In accordance with a further aspect of the present invention, an apparatus for bearing a liquid paste is disclosed. The apparatus includes a substrate having a first surface; and a hydrophilic layer disposed on the first surface, and having a plurality of protrusions, wherein the liquid sample on the hydrophilic layer have a contact angle therebetween ranging from 2 to 85 degrees.

Accordance with a further aspect of the present invention, a method of manufacturing a strip for an electronic device configured to sense a liquid sample is disclosed. The method comprises steps of: (a) providing a substrate having a first surface; (b) disposing a plurality of protrusions on the first surface; and (c) disposing a hydrophilic layer having a layer surface covering the first surface and the plurality of protrusions on the first surface and a second surface opposite to the layer surface, wherein: each of the plurality of protrusions has a width; and any adjacent two of the plurality of protrusions have a distance therebetween ranging from 0.5 to 100 times of the width.

The above objects and advantages of the present invention will become more readily apparent to those ordinarily skilled in the art after reviewing the following detailed descriptions and accompanying drawings, in which:

BRIEF DESCRIPTION OF THE DRAWINGS

FIGS. 6A to 6C show test results of the tests using specimen according to embodiments of the present invention.

DETAILED DESCRIPTION OF THE PREFERRED EMBODIMENT

Figure 1A:
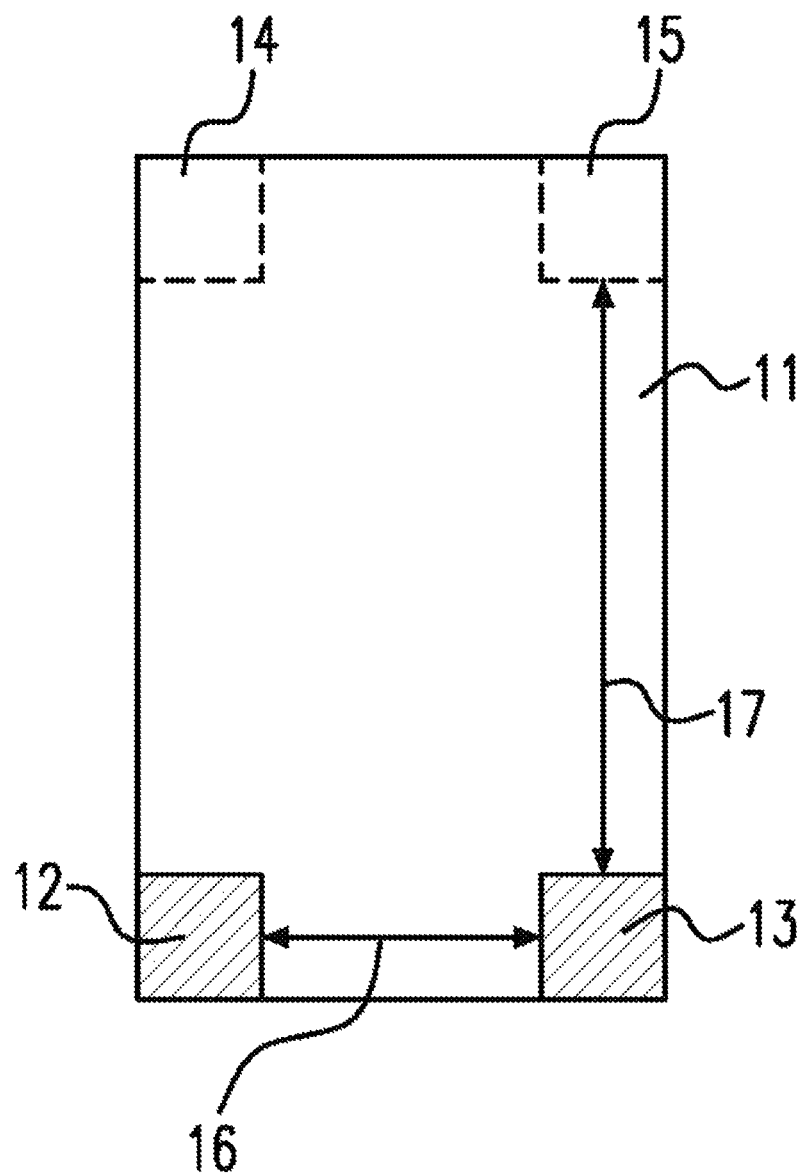
FIGS. 1A-1C show diagrams of a conducting package structure according to a preferred embodiment of the present invention processed.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

The present invention can be applied in the electronic packaging industry. The present invention utilizes the principles of the Wenzel model to design a conducting structure conforming to the Wenzel model, wherein the applied Wenzel model relates to the relationship between the surface tension of a droplet (that is, a colloid in the present invention) and the roughness of a substrate, wherein the roughness of the substrate can be achieved by employing patterning treatment on a surface of the substrate, wherein a specific surface area of the surface with the patterning treatment is increased, meaning that the roughness of the substrate is increased. The Wenzel model is the evolved version of the Young equation. The Young equation refers to the relationship of a contact angle of a liquid on a surface solid where three interfacial tensions balance. The Young equation is as shown in equation (1):

$$\gamma_{sg} = \gamma_{sl} + \gamma_{gl} \times \cos\theta \quad (1)$$

$\gamma_{sg}$ denotes solid-vapor interfacial tension; $\gamma_{sl}$ denotes solid-liquid interfacial tension; $\gamma_{gl}$ denotes vapor-liquid interfacial tension and $\theta$ denotes the angle at which the vapor-liquid interface meets the solid-liquid interface and is also called the contact angle. The contact angle is defined as the angle formed by the intersection of the vapor, liquid and solid phases contact point (geometrically acquired by applying a tangent along the vapor-liquid interface at the contact point between liquid and solid). In the present invention, the contact angle is also called the wetting angle, and is used to quantify the wettability. If $\theta<90°$, the surface of the solid phase is hydrophilic, the liquid phase has higher wettability on the surface of the solid phase. On the contrary, if θ>90°, the surface of the solid phase is hydrophobic, the liquid phase has lower wettability on the surface of the solid phase and is liable to move on the surface of the solid phase.

If a droplet is dropped on a rough solid surface, under the influence of the roughness, the Young equation will cause errors, and therefore, research with regard to the influence caused by roughness on the contact angle, such as the Wenzel model and the Cassie model, wherein the Wenzel model is shown as in equation (2).

$$\cos\theta = r(\gamma_{sg} - \gamma_{sl})/\gamma_{gl} = r\cos\theta_c \quad (2)$$

θ denotes a contact angle formed by the intersection at the contact point of the liquid on a smooth surface of a solid body. $\theta_c$ denotes another contact angle formed by the intersection at the contact point of the liquid on a rough surface of a solid body. $\gamma_{sg}$ denotes solid-vapor interfacial tension. $\gamma_{sl}$ denotes solid-liquid interfacial tension. $\gamma_{gl}$ denotes vapor-liquid interfacial tension. r denotes the roughness of the surface of the solid and is a ratio of actual contact area to apparent contact area, r≥1. When the surface of the solid body is hydrophobic, $\cos\theta_c<0$ and $90°<\theta_c<180°$, then $\cos\theta<\cos\theta$, and $\theta>\theta_c$. When the surface of the solid body is hydrophilic, $\cos\theta_c>0$ and $0°<\theta_c<90°$, then $\cos\theta>\cos\theta_c$ and $\theta_c$.

Furthermore, the present invention also refers to research with regard to a relationship between a liquid (such as a volatile chemical solvent, called solvent hereinafter) and body surface area dimension of surface of a solid body. When the solvent is disposed on the surface of the solid body, the solvent will be influenced by the structure of the solid body surface. For example, if the structure of the solid body surface has a plurality of triangular pyramids, it will guide the solvent in a specific diffusing direction and increase the diffusion rate of the solvent; if the structure of the solid body surface has a plurality of cylinders or pillars of any other shape, compared to the structure of the solid body only having a planar surface, it will have larger total body surface area causing the diffusible area of the solvent to increase, also increasing the rate of volatilization of the solvent. Therefore, it can be seen that the total body surface area of the solid body surface is in direct proportion to the rate of volatilization of the solvent.

As described above, we conclude that by changing the roughness of the solid body surface, we can determine the contact angle of the liquid on the solid body surface and thereby change the wettability of the solid body surface. The present invention utilizes this principle for SMT technology for electronic packaging, the dispensing technique and the dot control technique to cause an adhesive material used for pasting to have a surface tension when it is placed on the surface of the post-patterning treatment substrate, and further to cause the adhesive material to have a wetting angle on the substrate and appear as a semicircular shape. In addition, according to the fact that the surface of the substrate is characterized by a roughness (conforming to the Wenzel model) after the patterning treatment, there is an interfacial tension generated between the adhesive material and the surface of the substrate, confining the adhesive material to a certain position. Furthermore, the present invention further utilizes another roughness (simply increases the total specific surface area of the solid body surface) to accelerate the volatilization of the solvent of the adhesive material and control the diffusion degree of the solvent. Therefore, the shape and position of an adhesive material used for pasting presented in the present invention are consistent with the shape and position of the surface of the post-patterning treatment substrate, further to cause the electronic device to past with no deviation, thus achieving high stability and product capacity with a high yield factor.

The concepts of the present invention are illustrated below.

Figure 1B:
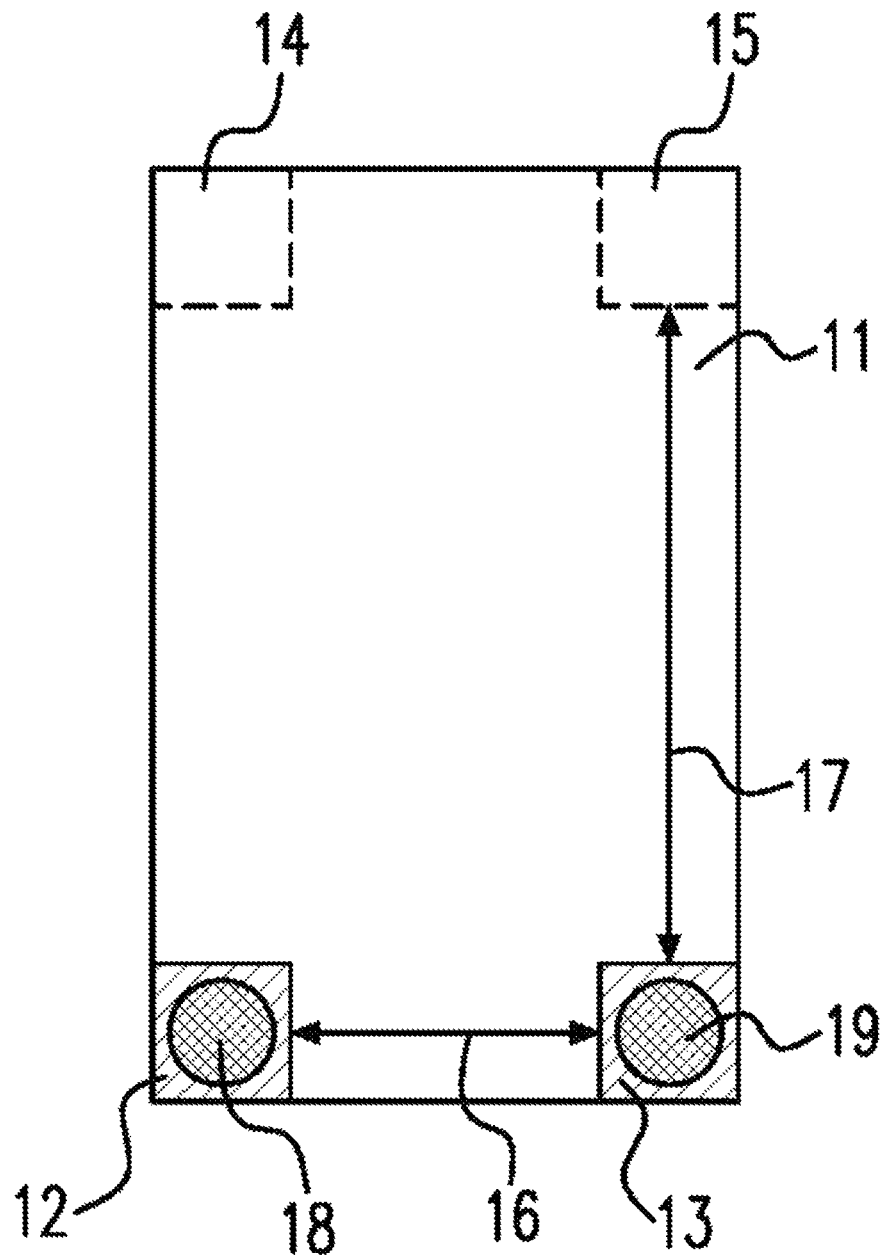
Figure 1C:
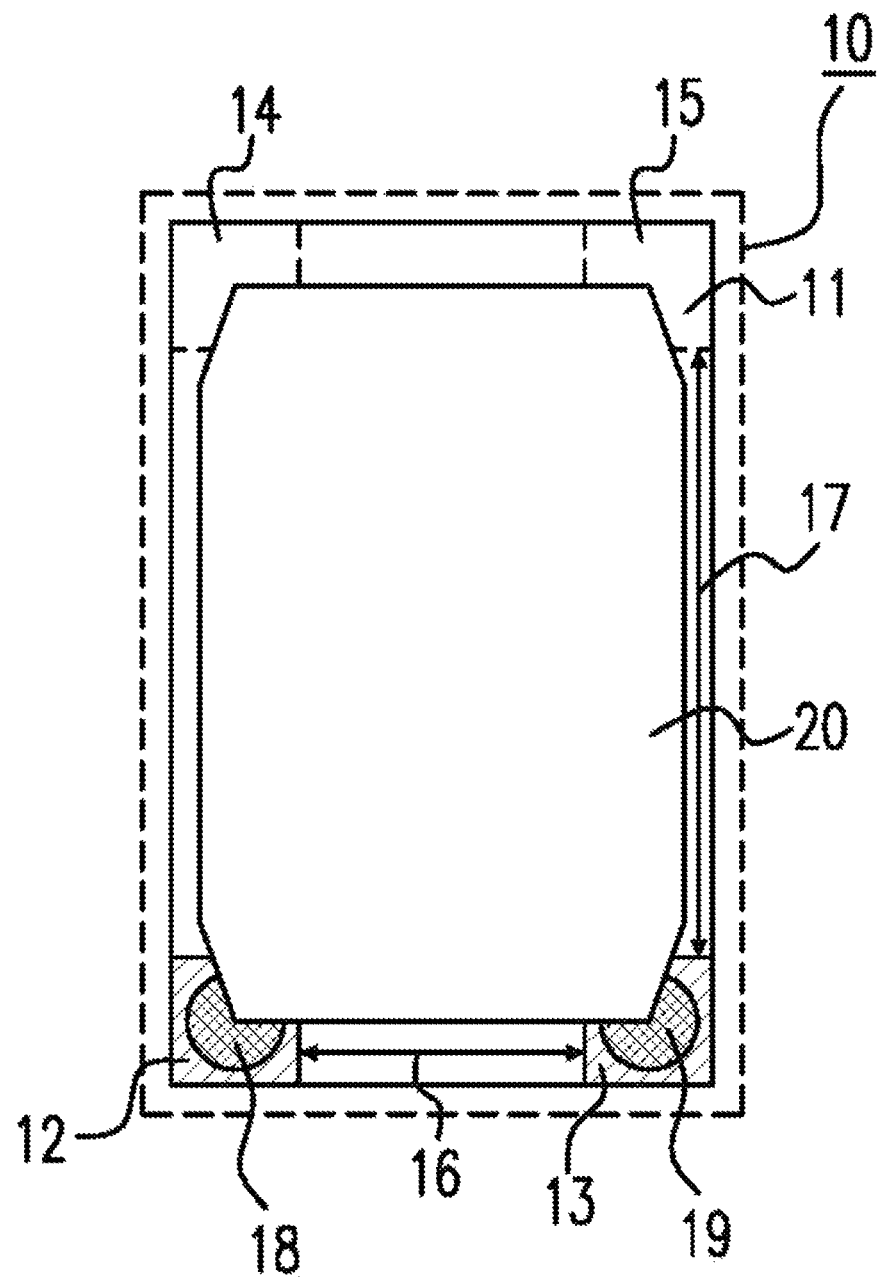

Please refer to FIGS. 1A, 1B and 1C, which respectively show diagrams of a conducting package structure according to a preferred embodiment of the present invention processed during a first state, a second state, and a third state. As shown in FIG. 1C, the conducting package structure processed during the third state includes a substrate 11, at least a conducting structure 12 (and optional conducting structures 13, 14, and 15), at least a glue material 18 (and an optional glue material 19), and an electronic device 20, wherein each conducting structure includes a conducting pad.

The process of the conducting package structure according to the present invention is mainly divided into Step 1 and Step 2. As shown in FIG. 1A, Step 1 performs a pretreatment on the substrate. As shown in FIGS. 1B and 1C, Step 2 binds the electronic device 20 to the substrate 11. With regard to Step 1, FIG. 1A shows a conducting material (such as: copper, gold, silver, or any other conductor) first being deposited or coated on the substrate 11 and etched to form the conducting structures 12, 13, 14 and 15. As shown in FIG. 1B, the conducting structures 12, 13, 14 and 15 separately have a plurality of patterned surfaces (not shown), wherein the plurality of patterned surfaces is formed according to the Wenzel model and increases the total specific surface area of the surface. That is, a primary structure of the plurality of patterned surfaces conforms to the Wenzel model and a secondary structure thereof is a surface structure having a relatively increased specific surface area. The details of the patterned surface will be described in detail below. As shown in FIG. 1B, in Step 2, the glue materials (or colloids) 18 and 19 are respectively dispensed on the conducting structure 12 and the conducting structure 13, 14 or 15. For example, the conducting structures 14 and 15 may be dispensed with two glue materials (not shown) thereon for fixing the electronic device 20. As shown in FIG. 1C, the conducting structures (also referred to as the conducting pad) 12 and 13 respectively limit a formed shape and a formed position of the glue materials 18 and 19. Under the condition that the glue materials 18 and 19 have a specific shape and a specific position, the electronic device 20 is disposed on the glue materials 18 and 19 to complete a conducting package structure 10.

In one preferred embodiment, the substrate 11 includes a ceramic substrate, a printed circuit board or any other form of electronic substrate. The conducting structures 12 and 13 separately have two patterned surfaces, and the two patterned surfaces may be for limiting the shape and position of the glue materials 18 and 19 respectively. The conducting structures 12 and 13 separately include two or more patterned surfaces (as shown in FIGS. 2A-2F), wherein the patterned surfaces are formed using a photolithography process, a dry-film photo-resister process, a screen printing process or any other film formation process. All of the glue materials 18 and 19 include a polymer, an organic material, a catalyst, a binding agent or a combination thereof. The electronic device 20 includes an integrated circuit, a capacitance, a transistor, a resistance or a quartz.

In one preferred embodiment, the substrate 11 at least includes a conducting structure (e.g., the conducting structure 12). For example, the conducting structures 12, 13, 14 and 15 are symmetrically disposed on the substrate 11.

In one preferred embodiment, as shown in FIG. 1C, the substrate 11 includes the conducting structures 12, 13, 14 and 15. The conducting structure 12 and the conducting structure 13 have therebetween a first distance 16, the conducting structure 13 and the conducting structure 15 have therebetween a second distance 17, and the second distance 17 is larger than the first distance 16. The conducting structures 12 and 15 are disposed on the diagonal corners of the substrate 11, so as to stably connect with the electronic device 20 because of the corresponding glue materials 18 and 19.

Figure 2A:
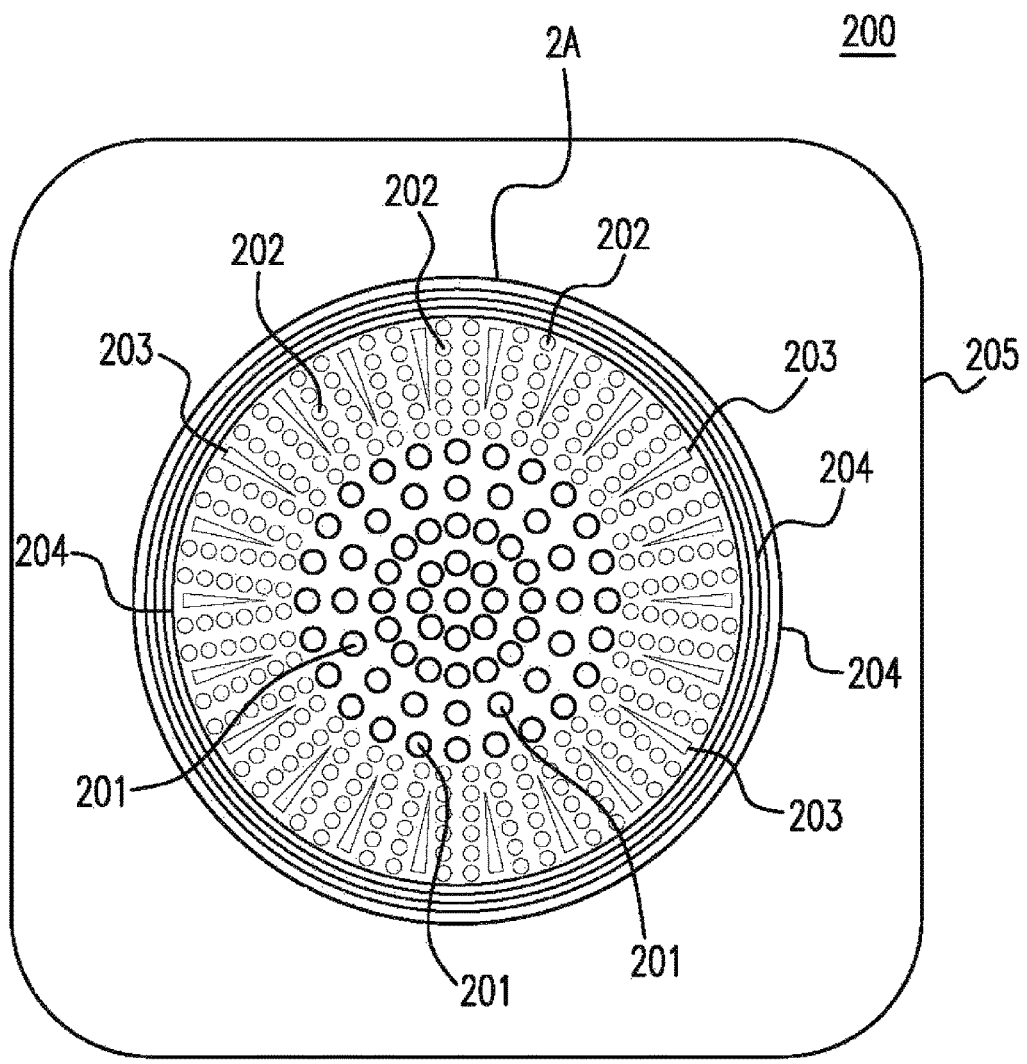
FIG. 2A shows a top view of a conducting structure with a patterned surface according to a preferred embodiment of the present invention processed.

Please refer to FIG. 2A, which shows a top view of a conducting structure 200 with a patterned surface 2A. In one preferred embodiment, a conducting structure 200 includes a conducting pad 205 (e.g., copper, gold, silver, or any other conductor), a plurality of guide rods 201, and a first auxiliary structure and a second auxiliary structure 204. Wherein, the first auxiliary structure includes a plurality of cylinders 202 and a plurality of triangular pyramids 203, and the second auxiliary structure 204 is a plurality of concentrically circular pieces 204. Wherein, the plurality of guide rods 201 is designed to conform to the Wenzel model, and the plurality of cylinders 202 and the plurality of triangular pyramids 203 conform to a principle of increasing a total specific surface area of a surface structure of the conducting pad 205. Therefore, the conducting structure 200 limits a dot (not shown) of a glue material by the plurality of guide rods 201, accelerates a volatilization of a solvent of the glue material and the diffusing direction of the solvent (not shown) by the plurality of cylinders 202 and the plurality of triangular pyramids 203, and controls the diffusing degree of the solvent by the plurality of concentrically circular pieces 204, i.e., the plurality of concentrically circular pieces 204 is used to retard an overflow of the solvent.

Figure 2B:
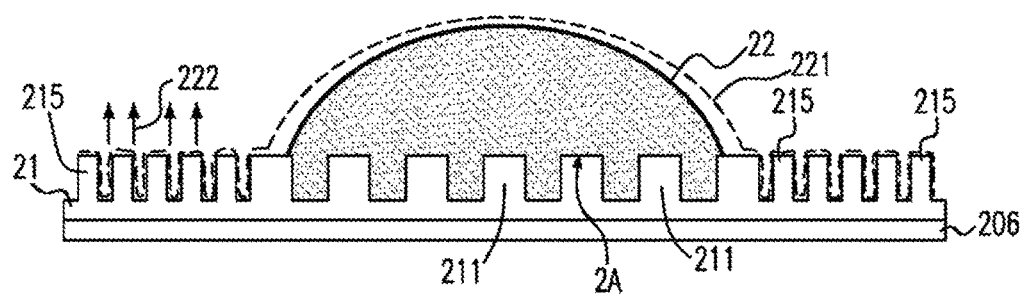
FIG. 2B shows a side view of a glue material and a relationship of a solvent of the glue material and a conducting structure.

Please refer to FIG. 2B, which shows a side view of a glue material (or a colloid) 22 and a relationship of a solvent 221 of the colloid 22 and a conducting structure 21 with a patterned surface 2A. In one preferred embodiment, the patterned surface 2A is formed with a plurality of guide rods 211 and a plurality of cylinders 215. The conducting structure 21 is disposed on a substrate 206 and limits a dot of a glue material 22 by the plurality of guide rods 211, i.e., the plurality of guide rods 211 of the conducting structure 21 generate an enhanced mutual interfacial tension on the dispensed glue material 22 to limit the glue material 22 to a certain region. Furthermore, the total specific surface area of the conducting structure 21 is increased by the plurality of cylinders 215. The solvent 221 diffused from the colloid 22 and the surface of the plurality of cylinders 215 form a gas-solid interface and so a vaporization phenomenon 222 appears on the surface of the plurality of cylinders 215. Because the plurality of cylinders 215 are dense arrays to increase a diffusible specific surface area of the solvent 221, the vaporizing rate of the solvent 221 is accelerated. Wherein, any two adjacent guide rods 211 of the plurality of guide rods 211 have therebetween a first distance 231, each guide rod 211 has a second distance 232 of width and a third distance 233 of height, and a first proportional relationship of the first distance 231 and the second distance 232 conforms to the Wenzel model, as shown in FIG. 2D.

Figure 2C:
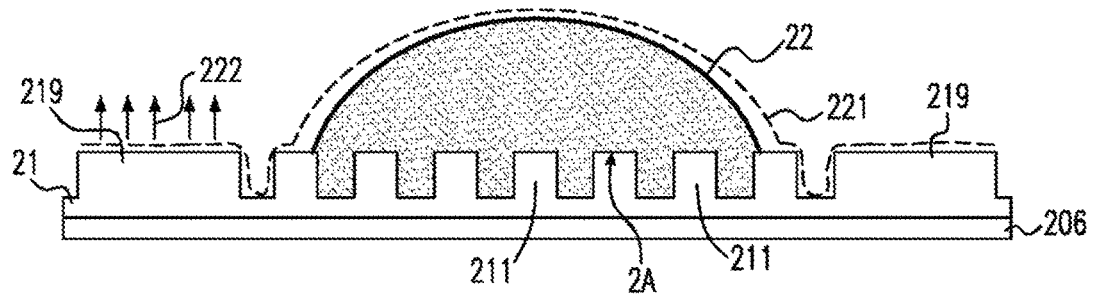
FIG. 2C shows another side view of a glue material and a relationship of a solvent of the glue material and a conducting structure.
Figure 2D:
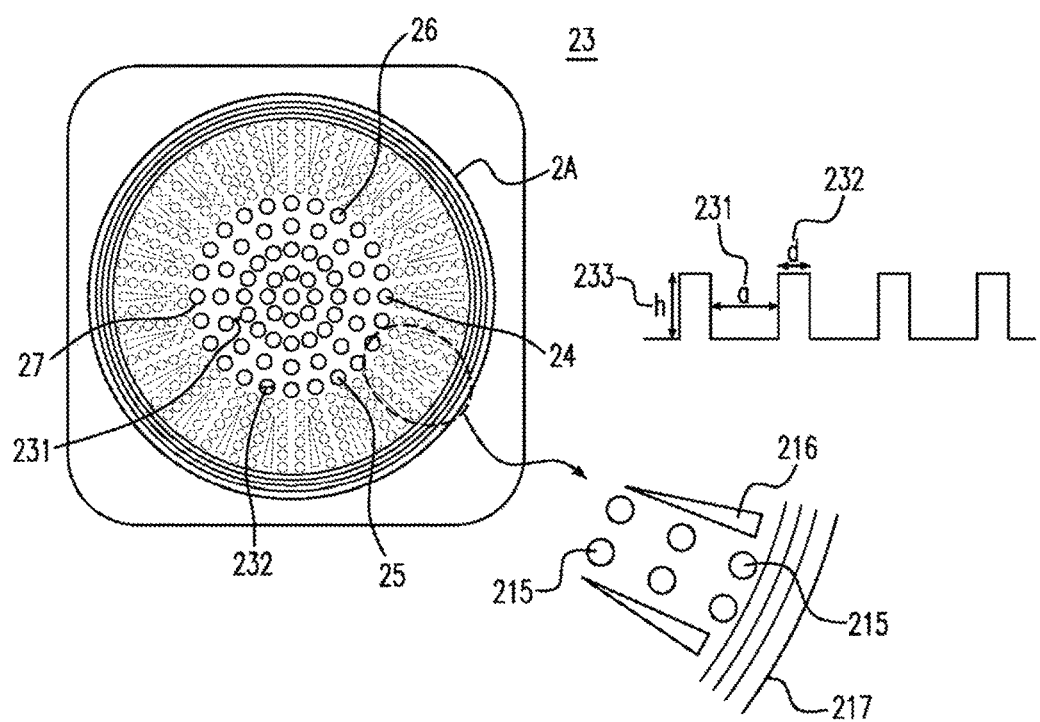
FIGS. 2D-2F show top views of conducting structures with different patterned surfaces according to a preferred embodiment of the present invention.

Please refer to FIG. 2C, which shows another side view of a glue material (or colloid) 22 and a relationship of a solvent 221 of the colloid 22 and a conducting structure 21 with a patterned surface 2A. In one preferred embodiment, the patterned surface 2A is formed with a plurality of guide rods 211 and a plurality of triangular pyramids 219. The conducting structure 21 is disposed on a substrate 206, and limits a dot of the colloid 22 by the plurality of guide rods 211, i.e., the plurality of guide rods 211 of the conducting structure 21 generate an enhanced mutual interfacial tension on the dispensed colloid 22 to limit the glue material 22 to a certain region. Moreover, the diffusing direction of the solvent 221 diffused from the colloid 22 is guided outward by the structure of the plurality of triangular pyramids 219. At the same time, a vaporization phenomenon 222 appears on a structure surface of the plurality of triangular pyramids 219 and so the vaporizing rate of the solvent 221 is accelerated. Wherein, any two adjacent guide rods 211 of the plurality of guide rods 211 have therebetween a first distance 231, each guide rod 211 has a second distance 232 of width and a third distance 233 of height, a first proportional relationship of the first distance 231 and the second distance 232 conforms to the Wenzel model, as shown in FIG. 2D.

In one preferred embodiment, as shown in FIGS. 2B and 2C, the plurality of guide rods 211, designed under the conditions that conform to the Wenzel model, can achieve the objective of the present invention. The conditions include a preset dimension relationship of A>2D (preferably A>>2D), wherein the distance 231 between any two adjacent guide rods is A, the width 232 of any of the two adjacent guide rods is D (the above-mentioned embodiments do not illustrate an effect of the height and only consider the effects of the A value and D value.)

In one preferred embodiment, as shown in FIGS. 2B and 2C, the plurality of cylinders 215, designed under the condition of increasing the specific surface area and guiding the direction of the solvent 221, can achieve the objective of the present invention. The condition includes dense arrays in any way on a surface structure in any form.

Figure 2E:
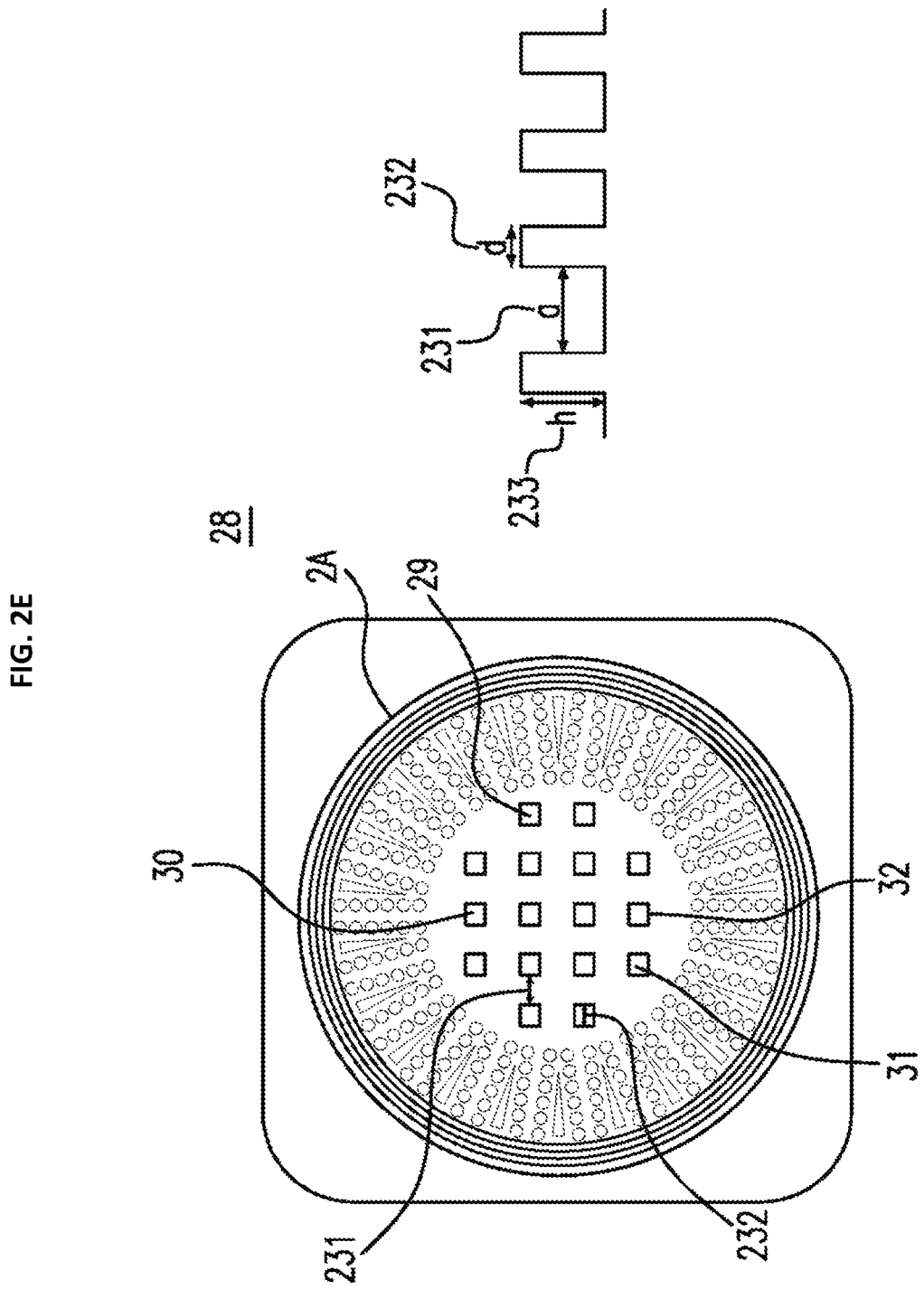
Figure 2F:
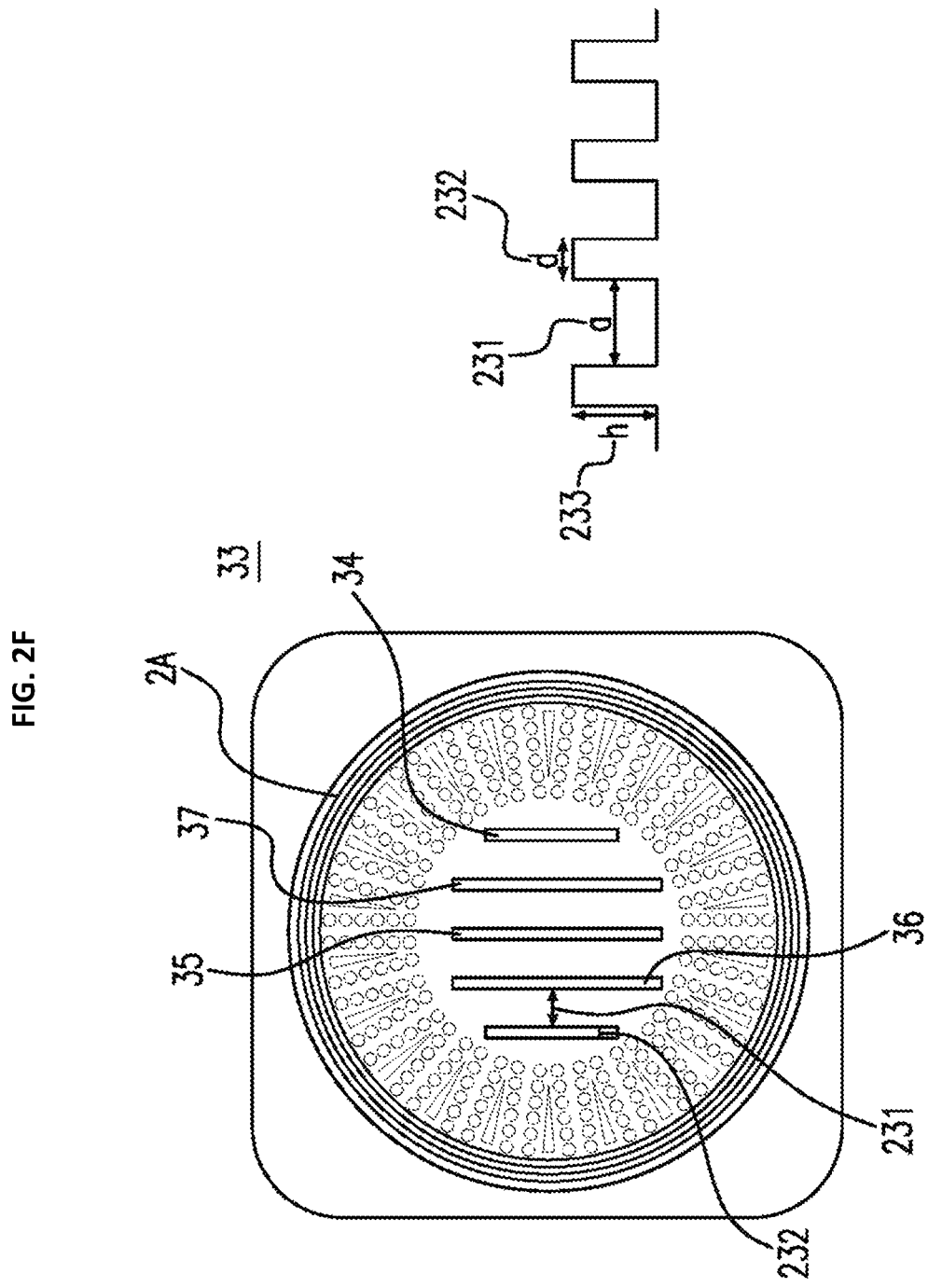

Please refer to FIGS. 2D-2F, which respectively show top views of the conducting structures 23, 28 and 33 with different patterned surfaces according to a preferred embodiment of the present invention. In one preferred embodiment, the conducting structures 23, 28 and 33 include a plurality of guide rods 24, 25, 26, 29, 30, 31, 34, 35 and 36, which have shapes in plan view of a circle 27, a square 32, a rectangle 37, an ellipse, any shape conforming to a proportional relationship or a combination thereof. The plurality of guide rods 24, 25, 26, 29, 30, 31, 34, 35 and 36 further include a plurality of dense cylinder arrays, a plurality of dense acicular arrays or a plurality of multi-layer dense cylinder arrays, or any structure conforming to this condition.

In one preferred embodiment, as shown in FIG. 2D, the first auxiliary structures 215 and 216, designed under a condition of increasing the specific surface area and being capable of direction guidance, can achieve the objective of the present invention. The condition includes dense arrays in any design on a surface structure in any form. For example, the first auxiliary structure further includes a cube, a cuboid, a cone, and any shape capable of increasing the specific surface area, and the dense arrays in any way further include a plurality of dense cylinder arrays, a plurality of dense acicular arrays or a plurality of multi-layer dense cylinder arrays; wherein the second auxiliary structure 217 determines the diffusing degree of the solvent.

In another preferred embodiment, the plurality of guide rods 24, 25, 26, 29, 30, 31, 34, 35 and 36 have a first total specific surface area, and the plurality of pillars 215 and 216 formed on the first auxiliary structure have a second total specific surface area, wherein the second total specific surface area is larger than the first total specific surface area.

Figure 3:
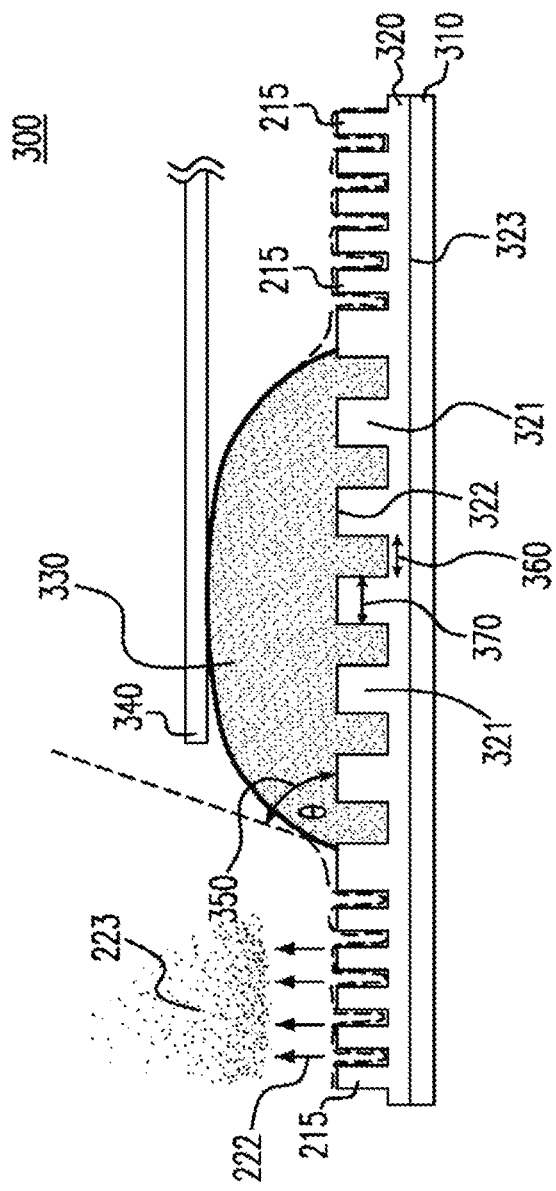
FIG. 3 is a side view of the conducting package structure according to a preferred embodiment of the present invention.

Please refer to FIG. 3, which is a side view of the conducting package structure according to a preferred embodiment of the present invention. The conducting package structure 300 includes a substrate 310, a conducting structure 320, a plurality of guide rods 321, a glue material 330 and an electronic device 340.

In one preferred embodiment, a method for manufacturing conducting package structure 300 includes the following steps. First, a conducting material (e.g., copper, gold, silver, or any other conductor) is deposited or coated on the substrate 310 and etched to form a conducting structure 320 with a patterned surface, wherein the conducting structure 320 includes a spatial structure and a patterned surface. Then, a glue material 330 is dispensed on the conducting structure 320 using a dispensing method, wherein a formed shape and a formed position of the glue material 330 are limited by the conducting structure 320 with the patterned surface, and a wetting angle 350 is between the glue material 330 and the conducting structure 320. Then, the electronic device 340 is disposed on the glue material 330 to complete a conducting package structure 300. For example, the patterned surface is formed with a plurality of guide rods 321.

In one preferred embodiment, the conducting structure 320 disposed on the substrate 310 conforms to the Wenzel model, and the conducting structure 320 has the patterned surface, which increases the roughness of the substrate 310. According to a reciprocal effect between a roughness of a surface and a droplet, as expressed by equation (2), it can be seen that the glue material 330 is dispensed on the substrate 310 with a rough surface, an interfacial tension is therebetween generated, and so the glue material 330 has a surface tension to fix the shape and position of the glue material 330.

In one preferred embodiment, the conducting structure 320 includes a spatial structure and has a patterned surface, wherein the patterned surface is formed with a plurality of cylinders 215, the plurality of cylinders 215 conforms to the feature of increasing the total specific surface area of the patterned surface. According to the design feature, it can be seen that when the solvent diffuses into the plurality of cylinders 215, an interfacial tension is therebetween generated and so the solvent has a surface tension to cause a vaporization phenomenon 222 on the surface of the plurality of cylinders 215, so as to diffuse the solvent in nebulized gas 223 into the environment.

In one preferred embodiment, the glue material 330 has a wetting angle 350 (contact angle θ) with the substrate due to the patterned surface, and the wetting angle 350 ranges from 15 to 85 degrees.

In one preferred embodiment, the glue material 330 on the substrate 310 has a surface tension, so as to shape the glue material 330 on the substrate 310 into a semicircle, wherein the glue material 330 has an acme for connecting with the electronic device 340.

In one preferred embodiment, the wetting angle 350 is determined by the patterned surface of the conducting structure 320 on the substrate 310. When the patterned surface has a preset dimensional relationship where any two adjacent guide rods have therebetween a distance larger than two times the width 370 of any of the two adjacent guide rods, the position and yield of the connected electronic device 340 are further controlled. In one preferred embodiment, the substrate 310 includes a ceramic substrate, a printed circuit board, or any other form of electronic substrate.

In one preferred embodiment, the conducting structure 320 includes a first surface 323 and a second surface 322 opposite to the first surface 323. The second surface 322 is formed with a plurality of guide rods 321. The conducting structure 320 may be for limiting the shape and position of the glue material 330.

In one preferred embodiment, the conducting structure 320 includes a first surface 323 and a second surface 322 opposite to the first surface 323. The second surface 322 is formed with a plurality of guide rods 321, a plurality of cylinders 202, a plurality of triangular pyramids 203 and a plurality of concentrically circular pieces 204 (as shown in FIG. 2A). One of the plurality of cylinders 202, the plurality of triangular pyramids 203 and the plurality of concentrically circular pieces 204 is made of a material selected from a conductor, e.g., copper, and a non-conductor, e.g., a polymer material.

In one preferred embodiment, the conducting structure 320 includes at least a conducting pad, wherein the conducting pad is formed using a photolithography process, a dry-film photo-resister process, a screen printing process or a film formation process.

In one preferred embodiment, the glue material 330 includes a polymer, an organic material, a catalyst, a binding agent or a combination thereof.

In one preferred embodiment, the dispensing method is a time-pressure dispensing method, a rotary dispensing method or a pump dispensing method.

In one preferred embodiment, the glue material 330 has enhanced interfacial tension on the conducting structure 320 of the substrate for fixing the position of the glue material 330. Moreover, because the conducting structure 320 causes the glue material 330 to have a surface tension, the surface tension holds the glue material in a semicircle, not any other shape.

In one preferred embodiment, the electronic device 340 includes an integrated circuit, a capacitance, a transistor, a resistance or a quartz.

The present invention discusses the relationship of the conducting structure (conducting pad) and the glue material, wherein, the primary structure conforms to the Wenzel model; and a secondary structure is a treatment for a conducting structure (conducting pad) on the substrate according to an effect principle of a specific surface area of a solid surface and a liquid disposed thereon. Therefore, the surface of the conducting structure has a structure capable of controlling the position and shape of the glue material to further solve the problems of a component (i.e., the electronic device) in adhering accuracy and available yield. However, the aforementioned patent discussed that the asymmetrical and lateral surface-tension forces between devices and a substrate are reduced by at least a conducting pad on the patterned substrate. Accordingly, it can be seen that the aforementioned patent researched into reducing the size of the conducting pad (i.e., reducing a distance along X direction) reduces the force of the X direction and so the resultant force of the X-Y directions is reduced to stabilize the connection of the electronic device and the substrate. Thus, the aforementioned patent discussed the relationship of a varying conducting pad and the electronic device, which is different from the relationship of the glue material and the conducting structure (conducting pad) with a patterned surface. One skilled in the art could not derive the techniques and the results of the present invention from the aforementioned patent.

Concepts of the present invention may also be applicable for the contact surface of a strip for an electronic device which is configured to sense a liquid sample such as water, sucrose solution, body fluid, glue material, soft material such as polymer and binding agent or blood. The same concept may also be applicable for apparatus designed for bearing a liquid or paste. When the liquid sample or paste is dropped on the strip, there is a need to create a hydrophilic contact surface to help the liquid sample extend to a larger area on the strip and therefore the liquid sample will move quickly and spread evenly to be tested. Please refer to FIG. 4A, which shows a schematic cross-sectional view of a liquid sample 450 on a strip 400 according to another embodiment of the present invention. After the liquid sample 450 is dropped on the strip 400, a contact angle θ can be observed at one edge of the liquid sample 450. It can be understood by the skilled person in the art that the patterned surface of the liquid sample may have significant influence on the contact angle θ.

Figure 4A:
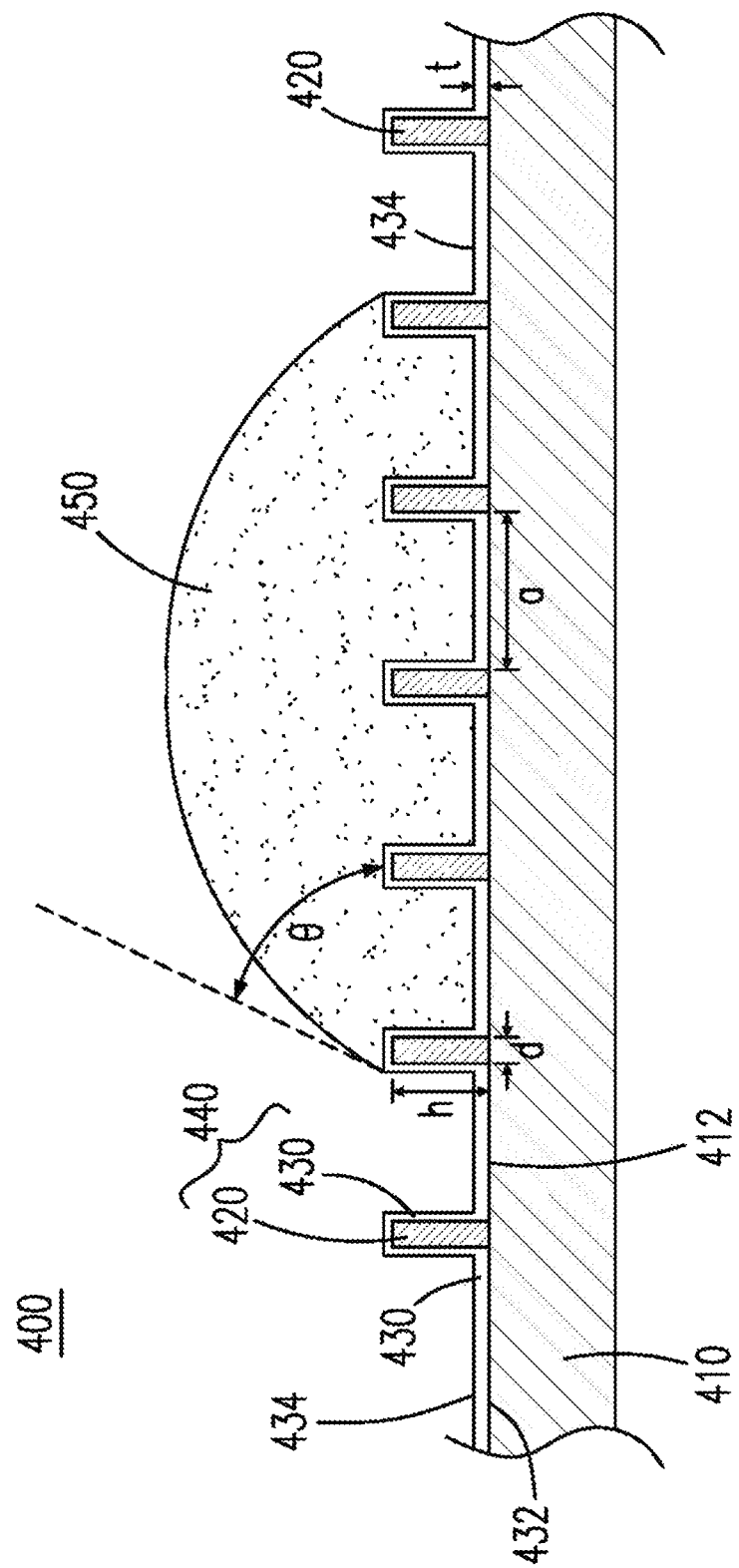
FIG. 4A is a schematic cross-sectional view of a liquid sample on a hydrophilic surface of the conducting package structure according to another embodiment of the present invention.

According to FIG. 4A, the strip 400 includes a substrate 410 which has a first surface 412, a plurality of protrusions 420 disposed on the first surface 412 and a hydrophilic layer 430 disposed on both the first surface 412 and the plurality of protrusions 420. Each of the plurality of protrusions 420 has a width d such as nominal width, mean width or average width. The hydrophilic layer 430 has a layer surface 432 disposed on and may also directly contact to the first surface 412 and the plurality of protrusions 420 and a second surface 434 opposite to the layer surface 432. According to another embodiment of the present invention, the plurality of protrusions 420 and the hydrophilic layer 430 may be formed of the same material, and thus they can be considered together as a contact layer 440. Each of the plurality of protrusions 420 also has a high h, which can be a nominal height, a mean height or an average height. The hydrophilic layer 430 has a thickness t which is very small compared to the width d and the height h of the protrusions 420, so the thickness t of the hydrophilic layer 430 can be neglected when considering the dimension of the pattern of the contact layer 440. In one embodiment, the hydrophilic layer 430 is formed of a conductive material such as metal. Any adjacent two of the plurality of protrusions 420 have a distance a therebetween ranging from 0.5 to 100 times of the width d. The skilled person in the art can understand that, the contact layer 440 of the strip 400 is hydrophilic when the contact angle θ is less than 90 degrees.

Figure 4B:
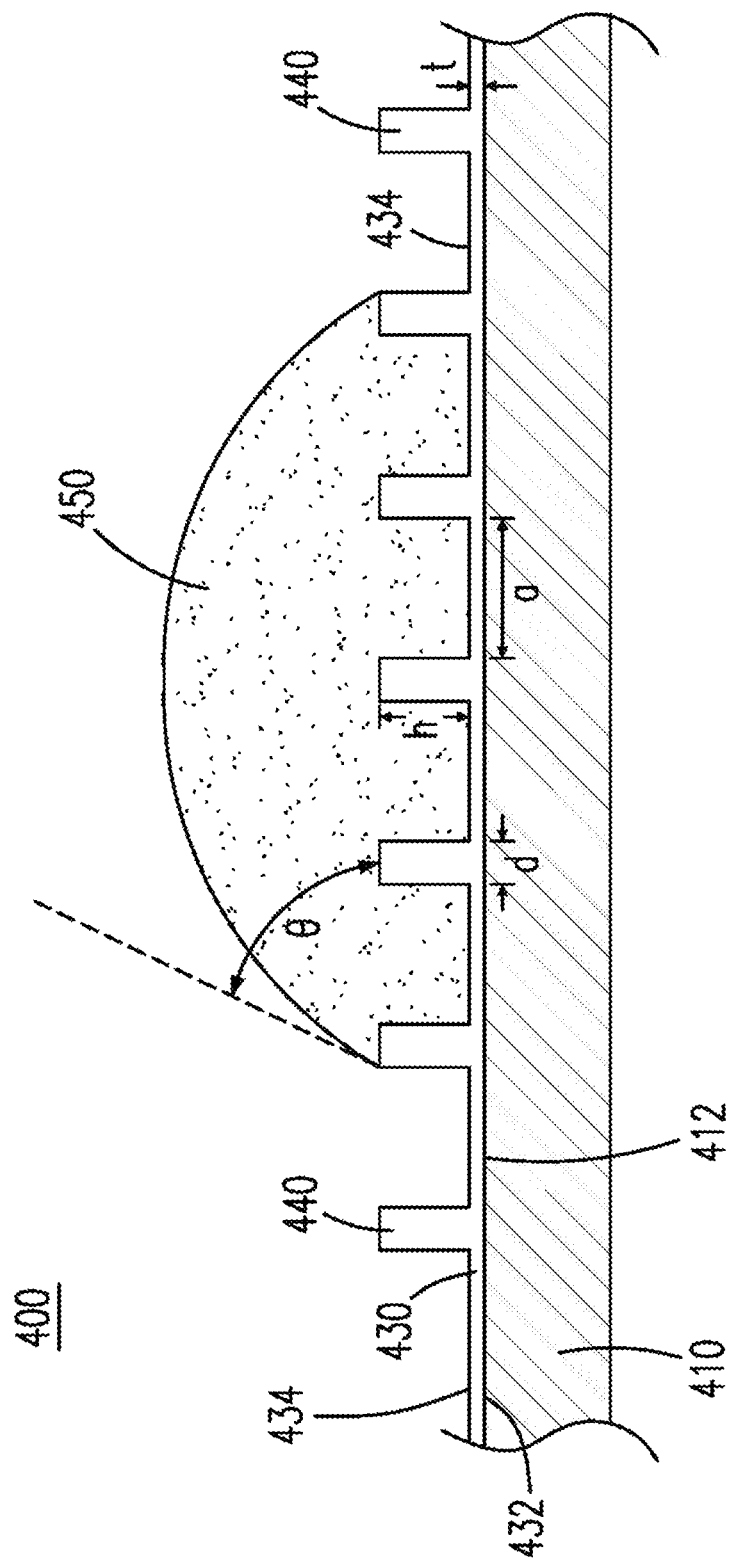
FIG. 4B is a schematic cross-sectional view of a liquid sample on a hydrophilic surface of the conducting package structure according to another embodiment of the present invention.

Please refer to FIG. 4B, which shows a schematic cross-sectional view of an apparatus such as a strip 400 for bearing a liquid sample or paste 450 according to another embodiment of the present invention. After the liquid sample 450 is dropped on the strip 400, a contact angle θ can be observed at one edge of the liquid sample 450. The strip 400 includes a substrate 410 having a first surface 412 and a hydrophilic layer 430 having a plurality of protrusions 440 disposed on the first surface 412. Each of the plurality of protrusions 440 has a width d such as nominal width, mean width or average width. The hydrophilic layer 430 has a layer surface 432 disposed on and may also directly contact to the first surface 412 and a second surface 434 opposite to the layer surface 432. Each of the plurality of protrusions 440 also has a high h, which can be a nominal height, a mean height or an average height. The hydrophilic layer 430 has a thickness t which is very small compared to the width d and the height h of the protrusions 440. In one embodiment, the hydrophilic layer 430 is formed of a conductive material such as metal, and any adjacent two of the plurality of protrusions 440 have a distance a therebetween ranging from 0.5 to 100 times of the width d.

Figure 4C:
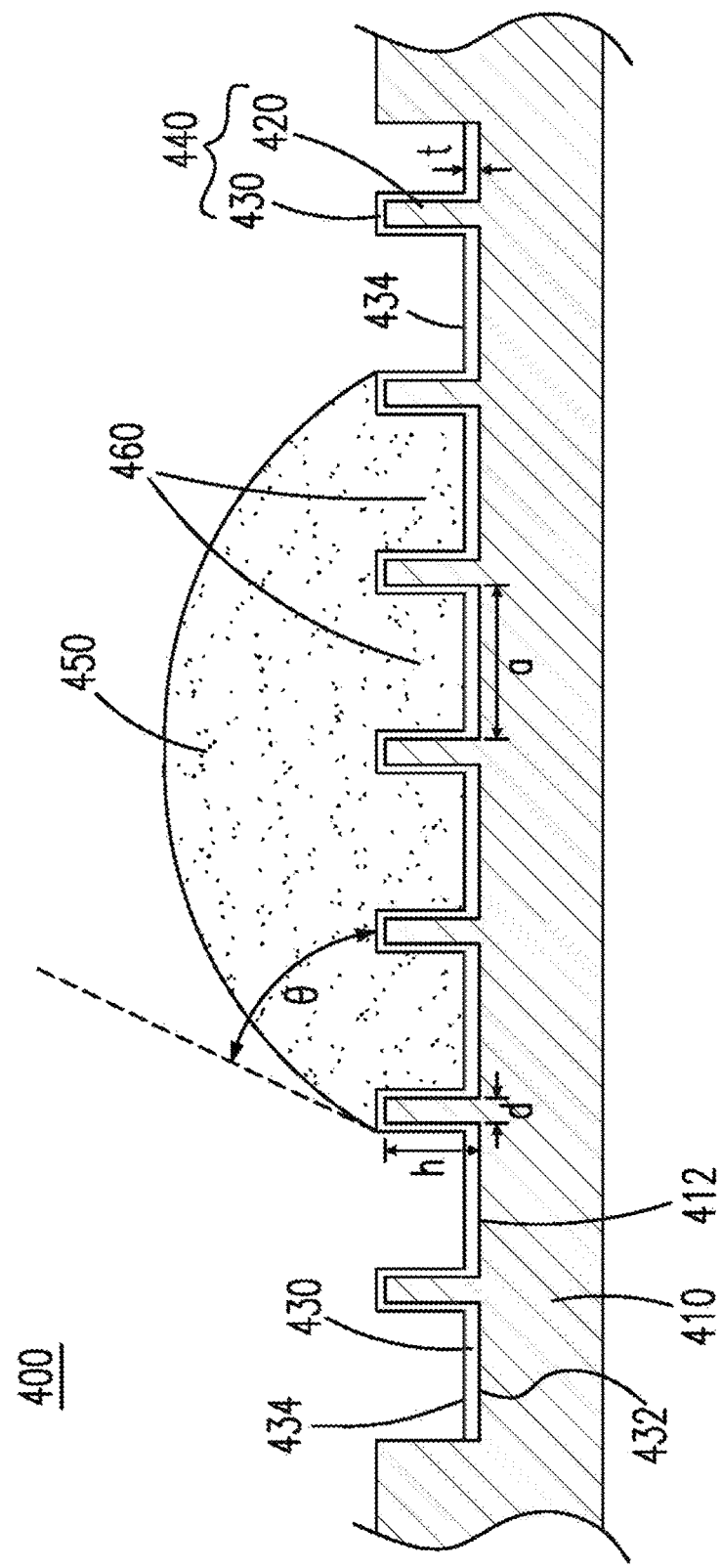
FIG. 4C is a schematic cross-sectional view of a liquid sample on a hydrophilic surface of the conducting package structure according to another embodiment of the present invention.

Please refer to FIG. 4C, which shows a schematic cross-sectional view of an apparatus such as a strip 400 for bearing a liquid sample or paste 450 according to another embodiment of the present invention. The strip 400 is formed on a substrate 410 with tranches 460 crisscross disposed on the first surface 412, and thus a plurality of protrusions 420 disposed on the first surface 412. a hydrophilic layer 430 disposed on both the first surface 412 and the plurality of protrusions 420. Each of the plurality of protrusions 420 has a width d such as nominal width, mean width or average width. The hydrophilic layer 430 has a layer surface 432 disposed on and may also directly contact to the first surface 412 and the plurality of protrusions 420 and a second surface 434 opposite to the layer surface 432. According to another embodiment of the present invention, the plurality of protrusions 420 and the hydrophilic layer 430 may be formed of the same material, and thus they can be considered together as a contact layer 440. Each of the plurality of protrusions 420 also has a high h, which can be a nominal height, a mean height or an average height. The hydrophilic layer 430 has a thickness t which is very small compared to the width d and the height h of the protrusions 420, so the thickness t of the hydrophilic layer 430 can be neglected when considering the dimension of the pattern of the contact layer 440. In one embodiment, the hydrophilic layer 430 is formed of a conductive material such as metal. Any adjacent two of the plurality of protrusions 420 have a distance a therebetween ranging from 0.5 to 100 times of the width d.

Figure 5A:
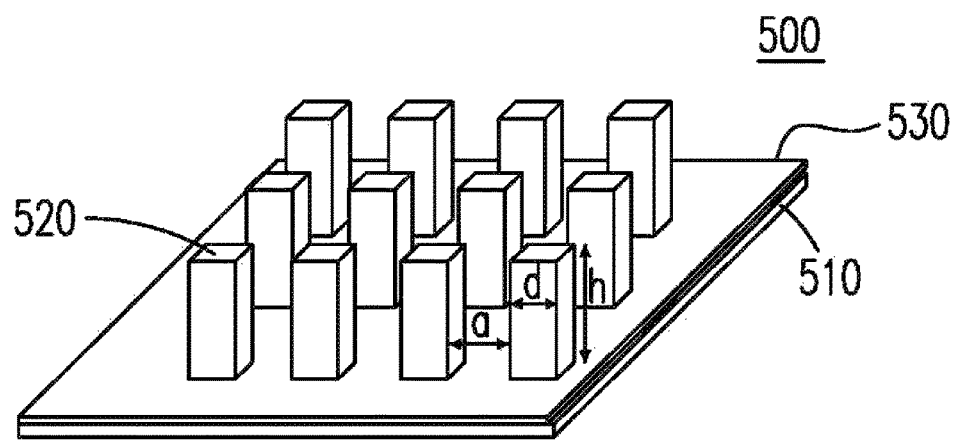
FIGS. 5A and 5B are schematic structure diagrams showing another embodiment of the present invention.

Please refer to FIG. 5A, which is a schematic structure diagram showing another embodiment of the present invention. A strip 500 for an electronic device configured to sense a liquid sample (not shown) comprises a substrate 510 and a hydrophilic layer 530 disposed on the substrate 510. The hydrophilic layer 530 includes a plurality of protrusions 520, each of which has a width d and a height h. It can be observed that the each of the plurality of protrusions 520 is a square column and the plurality of protrusions 520 form a square-column array.

Referring to Table 1, in some embodiments of the present invention, a ratio a/d of the distance a of any adjacent two of the plurality of protrusions 520 and the width d of the protrusions 520 ranges from 0.2 to 100 times of the width, wherein the height h and the width d of the protrusions 520 are about 50/1.5 and 10 micrometers respectively. The dimensions shown in Table 1 are applicable to the embodiments illustrated in FIGS. 4A-4C and FIG. 5A.

TABLE 1

(in micrometers except the ratio of a and d)

| | a/d | | | | | | | | |
|---|---|---|---|---|---|---|---|---|---|
| | 0.2 | 0.5 | 1 | 2 | 4 | 5 | 7 | 8 | 100 |
| a | 2 | 5 | 10 | 20 | 40 | 50 | 70 | 80 | 1000 |
| d | 10 | 10 | 10 | 10 | 10 | 10 | 10 | 10 | 10 |
| h | 50/1.5 | 50/1.5 | 50/1.5 | 50/1.5 | 50 | 50/1.5 | 50 | 50/1.5 | 50 |

Figure 5B:
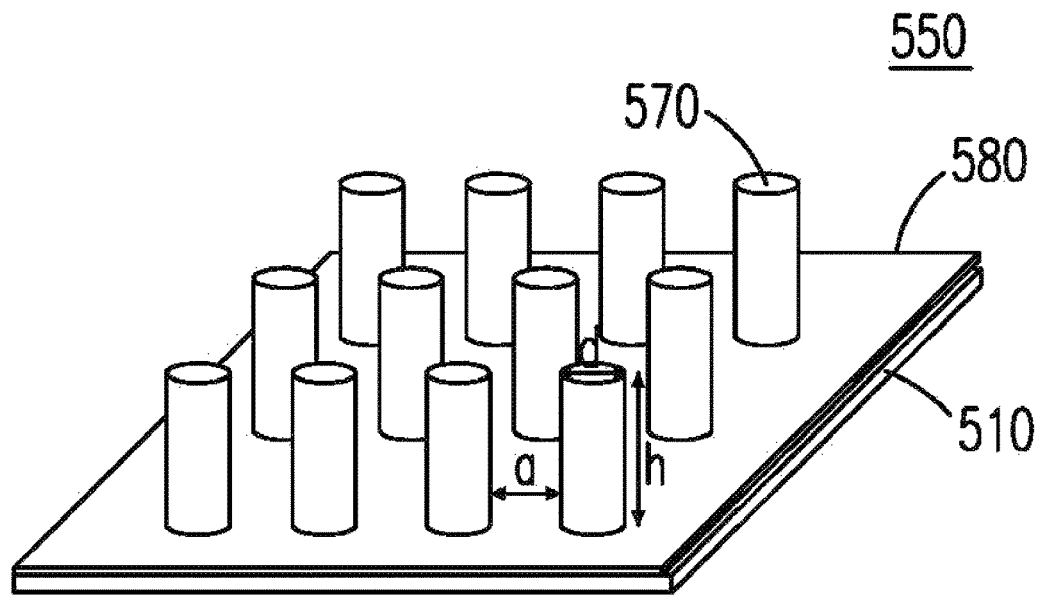

Please refer to FIG. 5B, which is a schematic structure diagram showing yet another embodiment of the present invention. A strip 550 for an electronic device configured to sense a liquid sample (not shown) comprises a substrate 510 and a hydrophilic layer 580 disposed on the substrate 510. The hydrophilic layer 580 includes a plurality of protrusions 570, each of which has a width d and a height h. It can be observed that the each of the plurality of protrusions 570 is a cylinder and the plurality of protrusions 570 form a cylinder array.

Referring to Table 2, in some embodiments of the present invention, a ratio a/d of the distance a of any adjacent two of the plurality of protrusions 570 and the width d of the protrusions 570 ranges from 2 to 100 times of the width, wherein the height h and the width d of the protrusions 570 are about 50 and 10 micrometers respectively. The width d may also be considered as the diameter of the cross-section of each of the cylinders. The dimensions shown in Table 2 may be applicable to the embodiments illustrated in FIGS. 4A-4C and FIG. 5B.

TABLE 2

(in micrometers except the ratio of a and d)

| | a/d | | | | | |
|---|---|---|---|---|---|---|
| | 2 | 4 | 8 | 16 | 32 | 100 |
| a | 20 | 40 | 80 | 160 | 320 | 1000 |
| d | 10 | 10 | 10 | 10 | 10 | 10 |
| h | 50 | 50 | 50 | 50 | 50 | 50 |

Notably, the width d and the height h can be considered as average values, mean values, median value or nominal values, when applicable.

Figure 6A:
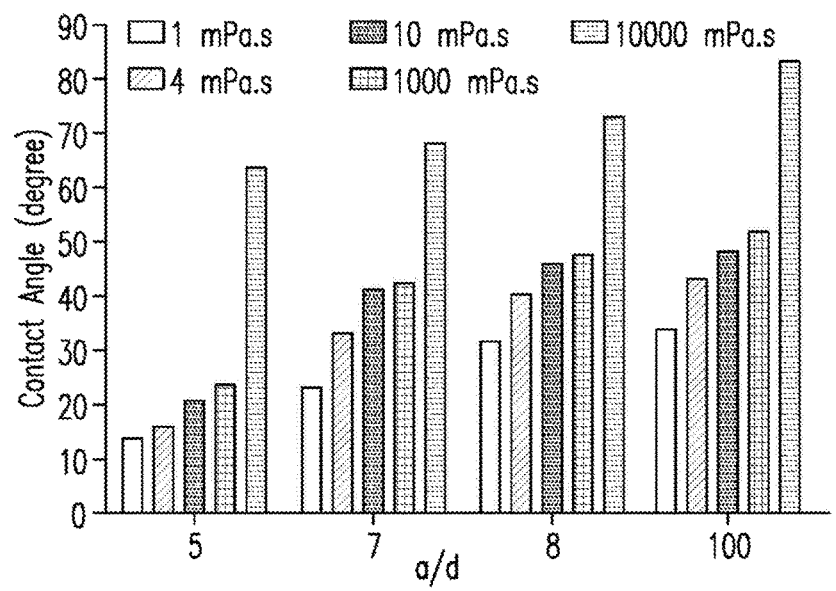

Please refer to FIGS. 6A and 6C, which show test results of the tests using specimen according to the embodiments illustrated in FIG. 5A. Specifically, the illustration shown in FIG. 6A is based on experimental data from the tests with specimens having protrusions 520 whose height h are 50 micrometers, while the illustration shown in FIG. 6C is based on experimental data from the tests with specimens having protrusions 520 whose height h are 1.5 micrometers. In FIG. 6A, there are totally 5 types of liquid samples which are water-based solutions containing sucrose of different percentages in weight for the test. Specifically, the concentrations of the 5 types of liquid samples are 0%, 20%, 40%, 75% and 78% of sucrose, which has viscosity (in mPa·s) of 1, 4, 10, 1000 and 10000 respectively. The viscosity of pure water is 1 mPa·s, and therefore these samples have viscosity ratios of 1:1, 1:4, 1:10, 1:1000 and 1:10000 respectively. Notably, the viscosity of human's blood is about 10 mPa·s, which is the same as that of the liquid sample of 40% concentration with sucrose. In FIG. 6C, there shows 4 types of water-based liquid samples with viscosity of 1, 4, 10 and 1000 respectively.

Again refer to FIG. 6A, it is observed that the contact angle ranges from 15 to 85 degrees when the liquid samples are placed on the hydrophilic layer of the test specimen. In particular, it is appreciated by the skilled person in the art that the contact angle ranges from 15 to 85 degrees when the viscosity of the liquid sample ranges from 1 to 10000 times of that of pure water and the ratio a/d ranges from 5 to 100 based on the description in the above paragraph, since the viscosity of the liquid sample with 78% of sucrose is 10000 times of that of pure water.

Please refer to 6B, which shows 4 types of water-based liquid samples with sucrose concentration of 0%, 20%, 40% and 75% respectively, using specimens according to the embodiments illustrated in FIG. 5B. Likewise, it can be appreciated that the contact angle ranges from 2 to 55 degrees when the viscosity of the liquid sample ranges from 1 to 1000 times of that of pure water, and the ratio a/d ranges from 2 to 100.

In FIG. 6C, it is observed that the contact angle ranges from 2 to 30 degrees when the liquid samples are placed on the hydrophilic layer of the test specimens.

Figure 6B:
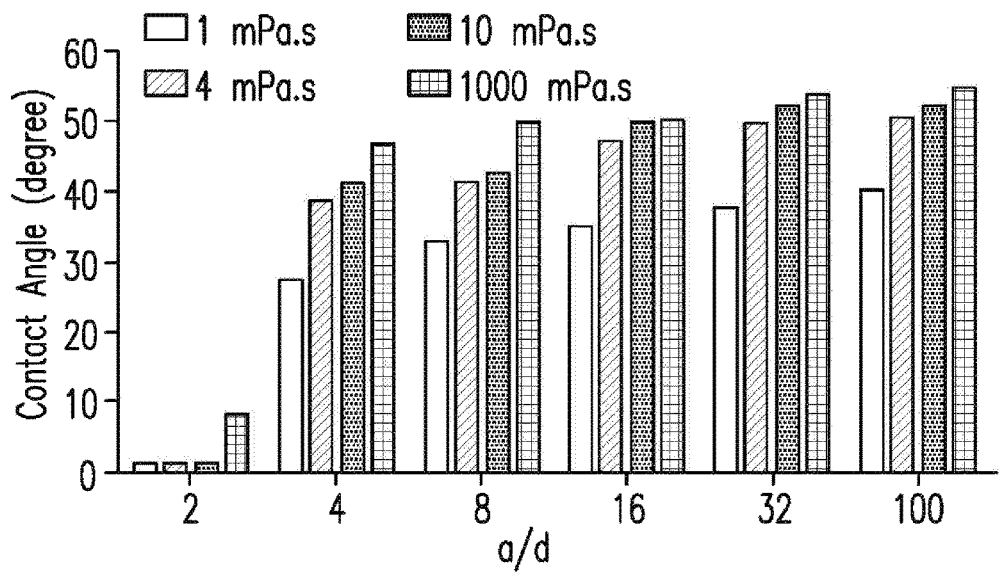

The test results can demonstrate that the device according to the present invention can serve as good hydrophilic layers for the contact surface of a strip for an electronic device which is configured to sense a liquid sample such as water, sucrose solution, body fluid or blood. When the liquid sample was dropped on the hydrophilic layer, it will move quickly along all directions of the surface of the hydrophilic layer and be ready to be sensed. For a liquid sample with viscosity which is 10 times of that of pure water such as blood, the contact angle ranges from 2 to 50 degrees according to the test results shown in FIGS. 6A-6C, which is a very efficient hydrophilic effect. Therefore, the present invention is of good use as a test strip to carry liquid samples such as body fluid or blood.

Embodiments

According to an embodiment of the present application, a method for manufacturing a conducting package includes: providing a substrate; forming a conducting structure on the substrate, wherein the conducting structure has a surface; patterning the surface to form a patterned surface; dispensing a glue material on the patterned surface, wherein a wetting angle between the glue material and the patterned surface is determined by the patterned surface; and disposing an electronic device on the glue material.

The conducting structure may include at least a conducting pad formed by one selected from a group consisting of a photolithography process, a dry-film photo-resister process and a screen printing process.

The glue material may be dispensed by one selected from a group consisting of a time-pressure dispensing method, a rotary dispensing method and a pump dispensing method.

The wetting angle may range from 15 to 85 degrees.

The patterned surface may conform to the Wenzel model.

According to an embodiment of the present application, the method may further include: providing a first auxiliary structure and a second auxiliary structure in the conducting structure, wherein the first auxiliary structure includes a plurality of cylinders and a plurality of triangular pyramids for determining the volatility and the diffusing direction of a solvent thereon; and the second auxiliary structure includes a plurality of concentrically circular pieces for determining the diffusing degree of the solvent.

According to an embodiment of the present application, a conducting package structure includes: a substrate, a conducting structure and a glue material, wherein: the conducting structure is formed on the substrate, and has a patterned surface; and the glue material is disposed on the patterned surface, wherein a wetting angle between the glue material and the patterned surface is determined by the patterned surface.

The conducting structure may include at least a conducting pad.

The conducting structure may further include: a first auxiliary structure configured to accelerate the volatilization of a solvent of the glue material; and a second auxiliary structure configured to retard the diffusion of the solvent.

The first auxiliary structure may include a plurality of cylinders and a plurality of triangular pyramids.

The second auxiliary structure may include a plurality of concentrically circular pieces.

The wetting angle may be an included angle between of the patterned surface and a tangent at a contact point between the glue material and the patterned surface, and the wetting angle ranges from 15 to 85 degrees.

The substrate may be one of a ceramic substrate and a printed circuit board and one of the first auxiliary structure and the second auxiliary structure is made of a material selected from one of a conductor and a non-conductor.

The glue material may include one selected from a group consisting of a polymer, an organic material, a catalyst, a binding agent, and a combination thereof.

The conducting structure may include a plurality of cylinder arrays, a plurality of acicular arrays and a plurality of multi-layer cylinder arrays.

An electronic device being one selected from a group consisting of an integrated circuit, a capacitance, a transistor, a resistance and a quartz may be disposed on the glue material.

According to an embodiment of the present application, a conducting package structure include: a substrate; and a conducting structure having a first surface disposed on the substrate and a second surface formed with a plurality of guide rods, wherein any two adjacent guide rods have therebetween a distance larger than two times of a width of any of the two adjacent guide rods.

The plurality of guide rods may include a structure being one selected from a group consisting of a plurality of cylinder arrays, a plurality of acicular arrays and a plurality of multi-layer cylinder arrays; the plurality of guide rods have a first total specific surface area; and the second surface is further formed with a plurality of pillars, and the plurality of pillars have a second total specific surface area, wherein the second total specific surface area is larger than the first total specific surface area.

According to an embodiment of the present application, a conducting package structure include: a substrate; and a conducting material formed with a first patterned structure, wherein the first patterned structure has a first surface disposed on the substrate and a second surface opposite to the first surface.

The second surface may include a primary structure and a secondary structure, the primary structure conforms to the Wenzel model, and the secondary structure has a relatively increased specific surface area of the second surface.

According to an embodiment of the present application, a strip for an electronic device configured to sense a liquid sample include: a substrate having a first surface; a plurality of protrusions disposed on the first surface, and each having a width; and a hydrophilic layer having a layer surface disposed on the first surface and the plurality of protrusions, and having a second surface opposite to the layer surface, whereby the liquid sample and the second surface have a contact angle therebetween ranging from 2 to 85 degrees when the liquid sample is disposed on the hydrophilic layer.

Any adjacent two of the plurality of protrusions may have a distance therebetween ranging from 0.5 to 100 times of the width, and each of the plurality of protrusions has a median height ranging from 1.5 to 50 micrometers, and the width is about 10 micrometers.

The liquid sample may be one selected from the group consisting of a water, a sucrose solution, a body fluid, a glue material, a soft material and a blood.

According to an embodiment of the present application, a strip for an electronic device configured to sense a liquid sample includes: a substrate having a first surface; and a hydrophilic layer disposed on the first surface, and having a plurality of protrusions, wherein: each of the plurality of protrusions has a width, and any adjacent two of the plurality of protrusions have a distance therebetween ranging from 0.5 to 100 times of the width.

Each of the plurality of protrusions may have a median height ranging from 1.5 to 50 micrometers, and the width is about 10 micrometers.

Each of the plurality of protrusions may have a shape of one of a cylinder, a triangular and a square column.

The contact angle therebetween may range from 2 to 85 degrees when a viscosity of the liquid sample ranges from 1 to 10000 times of that of a pure water.

The hydrophilic layer may be formed of a conductive material, and the plurality of protrusions form one of a cylinder array and a square-column array on the first surface.

The conductive material may be a metal.

Some of the plurality of protrusions may have a first shape of a cylinder and the others have a second shape of a square column.

According to an embodiment of the present application, an apparatus for bearing a liquid or paste, comprising: a substrate having a first surface; and a hydrophilic layer disposed on the first surface, and having a plurality of protrusions, wherein each of the plurality of protrusions has a width, and any adjacent two of the plurality of protrusions have a distance therebetween ranging from 0.5 to 100 times of the width.

The liquid sample and the second surface may have a contact angle therebetween ranging from 2 to 85 degrees.

Each of the plurality of protrusions may have a median height ranging from 1.5 to 50 micrometers, and the width is about 10 micrometers.

Each of the plurality of protrusions may have a shape of one of a cylinder, a triangular and a square column.

A method of manufacturing a strip for an electronic device configured to sense a liquid sample, comprising steps of: (a) providing a substrate having a first surface; (b) disposing a plurality of protrusions on the first surface; and (c) disposing a hydrophilic layer having a layer surface covering the first surface and the plurality of protrusions on the first surface and a second surface opposite to the layer surface, wherein: each of the plurality of protrusions has a width; and any adjacent two of the plurality of protrusions have a distance therebetween ranging from 0.5 to 100 times of the width.

Each of the plurality of protrusions may have a median height of ranging from 1.5 to 50 micrometers, and the width is about 10 micrometer.

Each of the plurality of protrusions may have a shape of one of a cylinder, a triangular and a square column.

In conclusion, the present invention utilizes a surface micro-processing for the surface to cause the surface of the substrate conform to the Wenzel model, so as to control the range of the contact angle between the semi-fluid glue material and electronic device. Thereby the relative positions among the substrate, the glue material and the packaged electronic device are fixed. The substrate with the surface micro-processing has a specific surface area to cause the organic solvent to diffuse and evaporate quickly. Thereby, the liquidity of the glue material after it is dispensed on the substrate is quickly reduced and the dot size of the glue material is shrunk. Thus, the present invention has the advantages of quickly and accurately assembling electronic devices and eliminating or decreasing the prebaking time.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A strip for an electronic device configured to sense a liquid sample, comprising:
a substrate having a first surface;
a plurality of protrusions disposed on the first surface, and each having a width; and
a hydrophilic layer having a conductive layer disposed on the first surface and the plurality of protrusions, and having a second surface opposite to the first surface, whereby the liquid sample and the second surface have a contact angle therebetween ranging from 2 to 50 degrees when the liquid sample is disposed on the hydrophilic layer, wherein any adjacent two of the plurality of protrusions have a distance therebetween ranging from 2 to 100 times of the width, and each of the plurality of protrusions has a median height ranging from 1.5 to 50 micrometers, and the strip achieves the contact angle in absence of a driving electrical voltage on the conductive layer.

2. A strip as claimed in claim 1, wherein the width is about 10 micrometers.

3. A strip as claimed in claim 1, wherein the contact angle therebetween ranges from 2 to 50 degrees when a viscosity of the liquid sample ranges from 1 to 10000 times of that of a pure water.

4. A strip as claimed in claim 1, wherein each of the plurality of protrusions has a shape of one of a cylinder, a triangular and a square column.

5. A strip as claimed in claim 1, wherein the plurality of protrusions form one of a cylinder array and a square-column array on the first surface.

6. A strip as claimed in claim 1, wherein the liquid sample is one selected from the group consisting of a paste, a glue material and a combination thereof.

7. A strip as claimed in claim 1, wherein the conductive layer is formed of a metal.

8. A strip as claimed in claim 1, wherein the liquid sample is one selected from the group consisting of a water, a sucrose solution, a body fluid, a soft material, a blood, and a combination thereof.

9. A strip as claimed in claim 1, wherein some of the plurality of protrusions have a first shape of a cylinder and the others have a second shape of a square column.

10. A strip for an electronic device configured to sense a liquid sample, comprising:
a substrate having a first surface; and
a hydrophilic layer disposed on the first surface, and having a plurality of protrusions, wherein:
each of the plurality of protrusions has a width,
any adjacent two of the plurality of protrusions have a distance therebetween ranging from 2 to 100 times of the width,
each of the plurality of protrusions has a median height ranging from 1.5 to 50 micrometers,
the hydrophilic layer is formed of a conductive material,
the liquid sample on the hydrophilic layer has a contact angle therebetween ranging from 2 to 50 degrees, and
the strip achieves a contact angle in absence of a driving electrical voltage on the hydrophilic layer.

11. A strip as claimed in claim 10, wherein the width is about 10 micrometers.

12. A strip as claimed in claim 10, wherein each of the plurality of protrusions has a shape of one of a cylinder, a triangular and a square column.

13. An apparatus for bearing a liquid sample, comprising:
a substrate having a first surface; and
a hydrophilic layer formed of a conductive material, disposed on the first surface, and having a plurality of protrusions, wherein the liquid sample on the hydrophilic layer have a contact angle therebetween ranging from 2 to 50 degrees when a viscosity of the liquid sample ranges from 1 to 10000 times of that of a pure water, each of the plurality of protrusions has a width of about 10 micrometers, any adjacent two of the plurality of protrusions have a distance therebetween ranging from 2 to 100 times of the width, each of the plurality of protrusions has a median height ranging from 1.5 to 50 micrometers, and the apparatus achieves the contact angle i n absence of a driving electrical voltage on the hydrophilic layer.

14. An apparatus as claimed in claim 13, wherein each of the plurality of protrusions has a shape of one of a cylinder, a triangular and a square column.

15. An apparatus as claimed in claim 13, wherein the liquid sample is one selected from the group consisting of, a water, a sucrose solution, a body fluid, a soft material, a blood and a combination thereof.

16. A strip as claimed in claim 1, wherein the liquid sample is one selected from the group consisting of a paste, a glue material and a combination thereof.

17. A strip as claimed in claim 1, wherein the liquid sample is a glue material.

* * * * *